US009563741B2

(12) United States Patent
Godbold et al.

(10) Patent No.: US 9,563,741 B2
(45) Date of Patent: Feb. 7, 2017

(54) CONSTRUCTING CUSTOM KNOWLEDGEBASES AND SEQUENCE DATASETS WITH PUBLICATIONS

(71) Applicant: Battelle Memorial Institute, Columbus, OH (US)

(72) Inventors: William Eugene Dunbar Godbold, Stanardsville, VA (US); Boyu Yang, Charlottesville, VA (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 323 days.

(21) Appl. No.: 14/280,285

(22) Filed: May 16, 2014

(65) Prior Publication Data
US 2015/0331993 A1    Nov. 19, 2015

(51) Int. Cl.
*G06F 15/18* (2006.01)
*G06F 19/28* (2011.01)
*G06N 5/02* (2006.01)
*G06F 19/24* (2011.01)
*G06F 19/22* (2011.01)

(52) U.S. Cl.
CPC .............. *G06F 19/28* (2013.01); *G06N 5/022* (2013.01); *G06F 19/22* (2013.01); *G06F 19/24* (2013.01)

(58) Field of Classification Search
None
See application file for complete search history.

(56) References Cited

U.S. PATENT DOCUMENTS

| 2011/0009476 | A1* | 1/2011 | McArthur | C12N 15/1048 514/44 R |
| 2012/0011428 | A1* | 1/2012 | Chisholm | G06F 17/241 715/230 |
| 2013/0157876 | A1 | 6/2013 | Lynch et al. | |
| 2013/0311875 | A1* | 11/2013 | Pappas | G06F 17/2247 715/234 |

FOREIGN PATENT DOCUMENTS

| WO | 2009137139 A9 | 11/2009 |
| WO | 2012027302 A2 | 3/2012 |

OTHER PUBLICATIONS

Lee et al. "Patome: a database server for biological sequence annotation and analysis in issued patents and published patent applications", Nucleic Acids Research, 2007, pp. 47-50.*

(Continued)

*Primary Examiner* — Li-Wu Chang
(74) *Attorney, Agent, or Firm* — Barnes & Thornburg LLP

(57) ABSTRACT

Illustrative embodiments of custom knowledgebases and sequence datasets, as well as related methods, are disclosed. In one illustrative embodiment, one or more computer-readable media may comprise a custom knowledgebase and an associated sequence dataset. The custom knowledgebase may comprise a plurality of assertions that have been automatically extracted from a plurality of publications, where each of the plurality of assertions encodes a relationship between a subject and an object. The sequence dataset may comprise a plurality of called biological sequences, where each of the plurality of called biological sequences is associated with one or more of the plurality of assertions of the custom knowledgebase.

17 Claims, 3 Drawing Sheets

(56) References Cited

OTHER PUBLICATIONS

S. Gupta et al., "ARG-ANNOT, a New Bioinformatic Tool to Discover Antibiotic Resistance Genes in Bacterial Genomes," Antimicrobial Agents and Chemotherapy, Oct. 21, 2013, pp. 212-220, vol. 58.
A. McArthur et al., "The Comprehensive Antibiotic Resistance Database," Antimicrobial Agents and Chemotherapy, Apr. 29, 2013, pp. 3348-3357, vol. 57.
Card: The Comprehensive Antibiotic Resistance Database, available at http://arpcard.mcmaster.ca/ (last visited Sep. 5, 2016).

* cited by examiner

CONSTRUCTING CUSTOM KNOWLEDGEBASES AND SEQUENCE DATASETS WITH PUBLICATIONS

TECHNICAL FIELD

The present disclosure relates, generally, to custom knowledgebases and sequence datasets and, more particularly, to custom knowledgebases and sequence datasets that may be used to interrogate biological sequence data from metagenomic samples.

BACKGROUND

A knowledgebase is a technology used to store complex structured and/or unstructured information that may be used by a computing device (e.g., a knowledge-based system or expert system) to deduce new information. Knowledgebases often represent their stored information using an object model (sometimes called an "ontology") with classes, subclasses, and instances. This ontology permits the representation of knowledge as a hierarchy of concepts with a particular domain, using a shared/controlled vocabulary to denote types, properties, and/or interrelationships associated with the information.

Some attempts have been made to develop knowledgebases in the areas of genetics and genomics. For instance, the Comprehensive Antibiotic Research Database (CARD), described in McArthur et al., "The Comprehensive Antibiotic Resistance Database," Antimicrobial Agents and Chemotherapy, vol. 57, pp. 3348-3357 (2013), includes data describing antibiotics and their targets along with antibiotic resistance genes, associated proteins, and antibiotic resistance literature. The CARD utilizes an Antibiotic Resistance Ontology (ARO) for the classification of antibiotic resistance gene data. Existing knowledgebases in the areas of genetics and genomics, however, have typically relied entirely on subject matter experts to manually construct the ontologies used by the knowledgebases.

SUMMARY

The present invention may comprise any one or more of the features recited in the appended claims, any one or more of the following features, and/or any combinations thereof.

According to one aspect, a method may comprise automatically extracting a plurality of assertions from a plurality of publications, wherein each of the plurality of assertions encodes a relationship between a subject and an object, manually editing the plurality of assertions automatically extracted from the plurality of publications to construct a custom knowledgebase for a particular biological field, and constructing a sequence dataset comprising a plurality of called biological sequences, wherein each of the plurality of called biological sequences is associated with one or more of the plurality of assertions of the custom knowledgebase.

In some embodiments, manually editing the plurality of assertions automatically extracted from the plurality of publications may comprise at least one of (i) selecting a subset of the plurality of assertions automatically extracted from the plurality of publications for inclusion in the custom knowledgebase, (ii) modifying the content of one or more of the plurality of assertions automatically extracted from the plurality of publications for inclusion in the custom knowledgebase, and (iii) creating one or more additional assertions for inclusion in the custom knowledgebase. The manual editing of the plurality of assertions automatically extracted from the plurality of publications may be performed by one or more subject matter experts in the particular biological field.

In some embodiments, automatically extracting the plurality of assertions from the plurality of publications may comprise utilizing natural language processing software to derive the plurality of assertions from the text of the plurality of publications. The plurality of publications may comprise peer-reviewed articles selected by the subject matter experts. The natural language processing software may be trained by the subject matter experts to recognize relevant assertions in the text of the plurality of publications. Each of the plurality of assertions may be expressed as a Resource Description Framework (RDF) triple.

In some embodiments, constructing the sequence dataset may comprise automatically extracting one or more called biological sequences from the plurality of publications. Constructing the sequence dataset may further comprise extracting additional called biological sequences from one or more publicly available databases, grouping the additional called biological sequences with the one or more called biological sequences automatically extracted from the plurality of publications in response to one or more predetermined resemblance criteria being met, and associating each group of called biological sequences with one or more of the plurality of assertions of the custom knowledgebase. The plurality of called biological sequences included in the sequence dataset and the associations between the plurality of called biological sequences and the plurality of assertions of the custom knowledgebase may be manually edited by the subject matter experts.

According to another aspect, one or more computer-readable media may comprise a custom knowledgebase comprising a plurality of assertions that have been automatically extracted from a plurality of publications, wherein each of the plurality of assertions encodes a relationship between a subject and an object, and a sequence dataset comprising a plurality of called biological sequences, wherein each of the plurality of called biological sequences is associated with one or more of the plurality of assertions of the custom knowledgebase.

In some embodiments, the plurality of assertions automatically extracted from the plurality of publications may have been manually edited by one or more subject matter experts in a biological field of the custom knowledgebase. The one or more computer-readable media may further a client application configured to compare a plurality of sample biological sequences to the plurality of called biological sequences of the sequence dataset and determine, for each sample biological sequence that resembles a called biological sequence of the sequence dataset, one or more probable characteristics associated with that sample biological sequence using one or more assertions of the custom knowledgebase that are associated with the called biological sequence that resembles that sample biological sequence.

In some embodiments, the plurality of called biological sequences of the sequence dataset comprise at least one of called biological sequences that provide resistance to one or more antibiotics and called biological sequences that mediate regulation of antibiotic resistance, and the plurality of assertions of the custom knowledgebase comprise assertions that encode relationships between the called biological sequences of the sequence dataset and at least one of antibiotic resistance elements and regulatory elements. The plurality of assertions of the custom knowledgebase may further comprise assertions that encode relationships between antibiotic resistance elements and particular resisted antibiotics.

According to yet another aspect, a method may comprise comparing a plurality of sample biological sequences to a plurality of called biological sequences included in a sequence dataset, retrieving, from a custom knowledgebase associated with the sequence dataset, one or more assertions that are associated with a called biological sequence of the sequence dataset that resembles one of the plurality of sample biological sequences, wherein the custom knowledgebase comprises a plurality of assertions that have been automatically extracted from a plurality of publications, each of the plurality of assertions encoding a relationship between a subject and an object, and determining one or more probable characteristics associated with the sample biological sequence that resembles the called biological sequence of the sequence dataset using the one or more assertions retrieved from the custom knowledgebase.

In some embodiments, the plurality of assertions automatically extracted from the plurality of publications may have been manually edited by one or more subject matter experts in a biological field of the custom knowledgebase. The method may further comprise generating the plurality of sample biological sequences using massively parallel sequencing of a metagenomic sample. Determining one or more probable characteristics associated with the sample biological may sequence comprise determining one or more antibiotics likely to be resisted. The method may further comprise generating a report that comprises a ranked listing of the antibiotics likely to be resisted.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
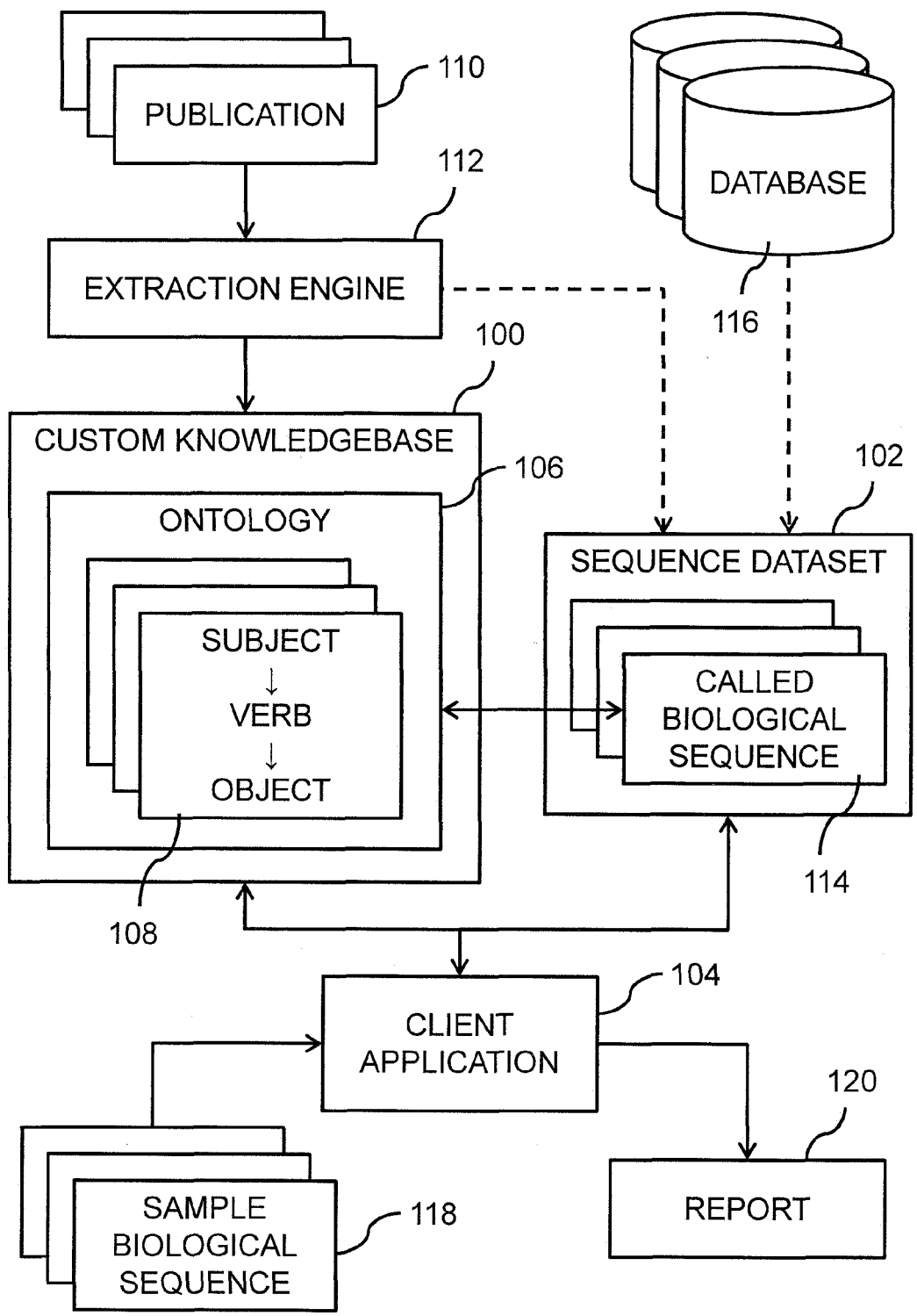
FIG. 1 is a simplified block diagram illustrating one embodiment of an environment including a custom knowledgebase, a sequence dataset, and a client application.

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the concepts described herein may be implemented in hardware, firmware, software, or any combination thereof. For instance, embodiments of the concepts described herein may be implemented as data and/or instructions carried by or stored on one or more machine-readable or computer-readable storage media, which may be read and/or executed by one or more processors. A machine-readable or computer-readable storage medium may be embodied as any device, mechanism, or physical structure for storing or transmitting information in a form readable by a machine (e.g., a computing device or system). For example, a machine-readable or computer-readable storage medium may be embodied as read only memory (ROM) device(s); random access memory (RAM) device(s); magnetic disk storage media; optical storage media; flash memory devices; mini- or micro-SD cards, memory sticks, and others.

In the drawings, specific arrangements or orderings of schematic elements, such as those representing devices, modules, software, and data elements, may be shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

In general, schematic elements used to represent software may be implemented using any suitable form of machine-readable instruction, such as software or firmware applications, programs, functions, modules, routines, processes, procedures, plug-ins, applets, widgets, code fragments and/or others, and that each such instruction may be implemented using any suitable programming language, library, application programming interface (API), and/or other software development tools. For example, some embodiments may be implemented using Java, C++, and/or other programming languages. Similarly, schematic elements used to represent data or information may be implemented using any suitable electronic arrangement or structure, such as a register, data store, table, record, array, index, hash, map, tree, list, graph, file (of any file type), folder, directory, database, and/or others.

Further, in the drawings, where connecting elements, such as solid or dashed lines or arrows, are used to illustrate a connection, relationship or association between or among two or more other schematic elements, the absence of any such connecting elements is not meant to imply that no connection, relationship or association can exist. In other words, some connections, relationships or associations between elements may not be shown in the drawings so as not to obscure the disclosure. In addition, for ease of illustration, a single connecting element may be used to represent multiple connections, relationships or associations between elements. For example, where a connecting element represents a communication of signals, data, instructions, or other information, it should be understood by those skilled in the art that such element may represent one or multiple signal paths, as may be needed, to effect the communication.

The present disclosure relates to custom knowledgebases and sequence datasets that are constructed and curated using semi-automated methods. In particular, the knowledgebase may comprise assertions that are automatically extracted from the professional literature and then manually edited by subject matter experts in the particular biological field to which the knowledgebase is directed. Similarly, the sequence dataset associated with the custom knowledgebase may comprise called biological sequences (e.g., nucleotide sequences, protein sequences, etc.) that are automatically extracted from the professional literature (as well as other public sources) and associated with the assertions of the custom knowledgebase, subject to manual editing by the subject matter experts. Using the presently disclosed methods, a custom knowledgebase and an associated sequence dataset for antibiotic resistance have been constructed. In that illustrative embodiment, the antibiotic resistance knowledgebase contains assertions automatically extracted from over 800 peer-reviewed articles, while the antibiotic resistance sequence dataset contains over 3,800 biological sequence types and over 250,000 individual biological sequences.

Once constructed, the custom knowledgebases and sequence datasets of the present disclosure may be used to interrogate biological sequences that are read from metagenomic samples. For instance, using the illustrative antibiotic resistance knowledgebase and sequence dataset, a client application can identify antibiotic resistance elements in sample biological sequences and report on what antibiotic drugs are likely to be resisted as a result of the identified antibiotic resistance elements. As such, the illustrative antibiotic resistance knowledgebase and sequence dataset may support microbial biothreat identification, surveillance, and/or analysis tools that are rapid, accurate, and/or field-accessible/deployable. Similarly, the illustrative antibiotic resistance knowledgebase and sequence dataset may also be used to implement real-time and accurate infectious disease decision support tools for clinicians at the point-of-care. While many of the features of the present disclosure will be described with reference to the illustrative embodiment of a custom knowledgebase and sequence dataset for antibiotic resistance, it is contemplated that custom knowledgebases and sequence datasets according to the present disclosure might also be constructed and utilized to interrogate biological sequences for any number of characteristics, including, but not limited to, virulence elements, hydrocarbon-degrading enzymes, visible characteristics (e.g., in human genomes), and race performance factors (e.g., in horse genomes).

Referring now to FIG. 1, one illustrative embodiment of an environment including a custom knowledgebase 100, a sequence dataset 102, and a client application 104 is shown as a simplified block diagram. The custom knowledgebase 100 represents the knowledge of a particular biological field (e.g., antibiotic resistance) and is organized around an ontology 106 that is specific to that biological field. In other words, the custom knowledgebase 100 organizes the information needed to understand and represent that particular biological field with reference to the professional literature.

In the illustrative embodiment, the custom knowledgebase 100 is embodied as data stored on one or more computer-readable media.

The custom knowledgebase 100 comprises a plurality of assertions 108, each of which encodes a relationship between a subject and an object, as illustrated in FIG. 1. In the illustrative embodiment, each of the assertions 108 is expressed as a Resource Description Framework (RDF) triple. As such, the assertions 108 have the form: subject→verb (or verb phrase)→object. The assertions 108 may encode any number of relationships, which will be dependent on the particular biological field represented by the custom knowledgebase 100 and the ontology 106 used. In the illustrative embodiment of the antibiotic resistance knowledgebase 100, by way of example, the assertions 108 may represent relationships such as "[subject] confers resistance to drug [object]," where the subject is a particular protein sequence or its encoding nucleotide sequence and the object is a particular antibiotic drug. The assertions 108 may also represent relationships with various antibiotic resistance elements and regulatory elements. For instance, some of the assertions 108 may encode a relationship between a biological sequence (or group of biological sequences) and an antibiotic resistance element or regulatory element, while other assertions 108 may encode a relationship between an antibiotic resistance element and a particular resisted antibiotic.

In the illustrative embodiment of the antibiotic resistance knowledgebase 100, the assertions 108 comprehensively describe the various classes of antibiotic resistance elements, including efflux pumps and their components, antibiotic inactivating enzymes, antibiotic target-altering enzymes, antibiotic target replacement proteins, proteins that result in reduced permeability to antibiotics, as well as sequence mutants that confer antibiotic resistance. The assertions 108 of the illustrative antibiotic resistance knowledgebase 100 also describe sequence elements that regulate expression of the types of resistance. Furthermore, the assertions 108 specify particular resisted antibiotic drugs for each type of antibiotic resistance. The relationships between the antibiotic resistance elements, regulatory elements, and antibiotic drugs are all described by the ontology 106.

As described in greater detail below (with reference to FIG. 2), the custom knowledgebase 100 is constructed and/or curated in a semi-automated manner. In particular, many of the assertions 108 of the custom knowledgebase 100 are generated automatically via extraction from a number of publications 110. In some embodiments, the publications 110 may be peer-reviewed articles from the relevant biological field that have been selected by subject matter experts in that field. As illustrated in FIG. 1, an extraction engine 112 may be used to digest the text of the publications 110 to derive the assertions 108 from the publications 110. For instance, the extraction engine 112 may analyze the text of the publications 110 for assertions 108 that fit the subject-relationship-object format and then encode each of these assertions 108 as an RDF triple. The assertions 108 derived by the extraction engine 112 may then be manually edited (e.g., by subject matter experts) to construct the custom knowledgebase 100. As discussed further below, this manual editing may involve associating an automatically extracted assertion 108 with a particular term of the ontology 106. It will be appreciated that, in contrast to prior art knowledgebases that have been generated by subject matter experts in an entirely manual fashion, the semi-automated construction and curation methods of the present disclosure offer significant time and cost savings and/or corresponding increases in the completeness of the custom knowledgebase 100.

The sequence dataset 102 comprises a plurality of called biological sequences 114 that are relevant to the biological field of the custom knowledgebase 100. In the illustrative embodiment, the sequence dataset 102 is embodied as data stored on one or more computer-readable media. Each of the called biological sequences 114 of the sequence dataset 102 is associated with one or more of the assertions 108 of the custom knowledgebase 100. In other words, each of the called biological sequences 114 is linked to one or more assertions 108 that describe that called biological sequence 114. In the illustrative embodiment, the called biological sequences 114 of the sequence dataset 102 are also grouped by types that may be described by the same assertion(s) 108. The associations between the called biological sequences 114 (or groups thereof) and the assertions 108 may be established automatically and/or manually by subject matter experts.

In the illustrative embodiment of the antibiotic resistance sequence dataset 102, the called biological sequences 114 include both called biological sequences 114 that provide resistance to one or more antibiotics and called biological sequences 114 that mediate regulation of antibiotic resistance. By way of example, the called biological sequences 114 of the antibiotic resistance sequence dataset 102 include protein sequences associated with resistance to particular antibiotics, as well as the encoding DNA sequences for those proteins. In some embodiments of the sequence dataset 102, some of the called biological sequences 114 may include adjoining or flanking sequences (in addition to the sequence elements directly associated with one or more assertions 108) to provide for more robust matching of sample biological sequences 118 to those called biological sequences 114.

Like the custom knowledgebase 100, the sequence dataset 102 may be constructed and/or curated in a semi-automated manner (as described in greater detail below with reference to FIG. 2). In particular, some of called biological sequences 114 of the sequence dataset 102 may be extracted from the publications 110 (in some embodiments, at the same time the assertions 108 are extracted from the publications 110). As illustrated in FIG. 1, the extraction engine 112 may be used to digest the text of the publications 110 to extract the called biological sequences 114 from the text. For instance, when the extraction engine 112 detects an assertion 108 in the one of the publications 110, the extraction engine 112 may then search for called biological sequences 114 set forth in the publication as examples of that assertion 108. The called biological sequences 114 found by the extraction engine 112 may then be manually edited (e.g., by subject matter experts) to construct the sequence dataset 102.

It is also contemplated that, in some embodiments, additional called biological sequences 114 may be automatically extracted from publically available databases 116 (e.g., National Center for Biotechnology Information (NCBI) databases) and added to the sequence dataset 102. As described in greater detail below (with reference to FIG. 2), these additional called biological sequences 114 may be compared to the called biological sequences 114 extracted from the publications 110 to determine whether they sufficiently resemble one another. If the additional called biological sequences 114 and the called biological sequences 114 extracted from the publications 110 meet certain predetermined resemblance criteria, they may be grouped together and associated with the same assertion(s) 108 in the custom knowledgebase 100.

The client application 104 interacts with the custom knowledgebase 100 and the sequence dataset 102 to infer information about sample biological sequences 118. The client application may receive the sample biological sequences 118 from any number of sources (e.g., as part of a FASTA or FASTQ format computer file). As described in greater detail below (with reference to FIG. 3), the client application 104 may be configured to compare the sample biological sequences 118 to the called biological sequences 114 of the sequence dataset 102. Where a sample biological sequence 118 sufficiently resembles one of the called biological sequences 114 included in the sequence dataset 102, the client application 104 may then use the assertion(s) 118 of the custom knowledgebase 100 that are associated with that called biological sequence 114 to determine one or more probable characteristics associated with that sample biological sequence 118. In other words, the client application 104 may utilize the knowledge represented by the custom knowledgebase 100 and the sequence dataset 102 to predict characteristics that will be expressed in the sample from which the sample biological sequences 118 were read.

The client application 104 may generate a report 120 summarizing the results of interrogating one or more sample biological sequences 118, including the probable characteristic(s) determined to be associated with those sample biological sequences 118. In some embodiments, the report 120 may include a ranked listing of antibiotics that are likely to be resisted by the sample from which the sample biological sequences 118 were read. By way of illustrative example, the report 120 may list a number of antibiotics beginning with those with the most resistance elements present in the sample and concluding with those with the fewest (or no) resistance elements present in the sample. In some embodiments, the report 120 might also include the minimum inhibitory concentrations for the listed antibiotics and even citations (and/or hyperlinks) to relevant publications. It will be appreciated that many other formats for the report 120 are possible.

In the illustrative embodiment, the client application 104 is embodied as software instructions stored on one or more computer-readable media (which may be executed by one or more processors). The client application 104 may provide a custom graphical user interface (GUI) to users of the custom knowledgebase 100 and the sequence dataset 102 that allows the users to create new reports, access old reports, store reports, and keep track of different cases based on particular metagenomic sequence samples.

Figure 2:
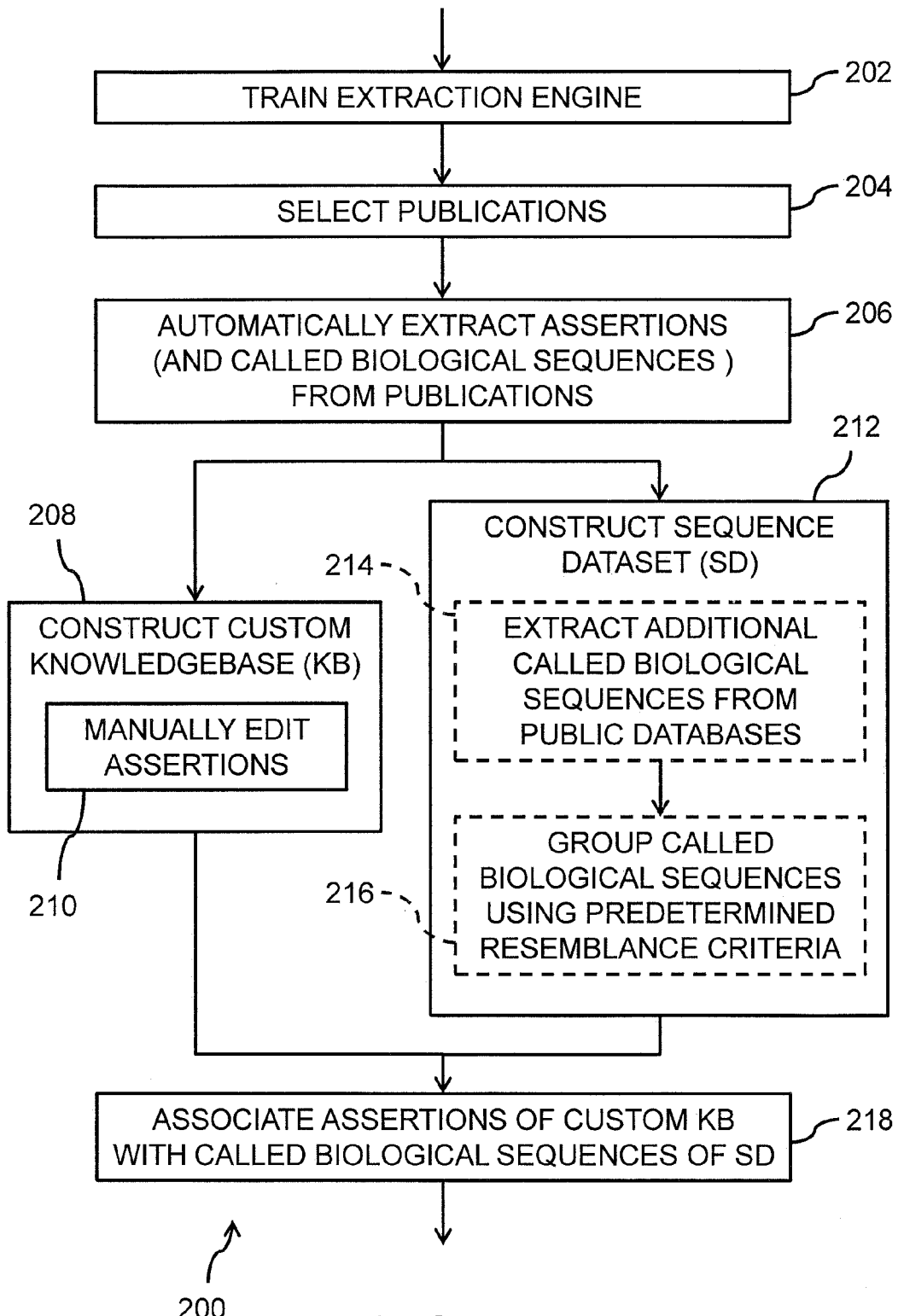
FIG. 2 is a simplified flow diagram illustrating one embodiment of a method of constructing the custom knowledgebase and the sequence dataset of FIG. 1.

Referring now to FIG. 2, one illustrative embodiment of a method 200 of constructing the custom knowledgebase 100 and the sequence dataset 102 is shown as a simplified flow diagram. The method 200 is illustrated as a number of blocks 202-218. Although the blocks 202-218 are generally shown and described sequentially in the present disclosure, it will be appreciated that the blocks 202-218 do not necessarily need to be performed in a particular order (unless otherwise noted below). For instance, it is contemplated that many of the blocks 202-218 might be performed in parallel with other blocks during the method 200.

The method 200 begins with block 202 in which the extraction engine 112 is trained to recognize assertions 108 relevant to a particular biological field in the text of the publications 110. In some embodiments, block 202 may involve subject matter experts (and/or others) providing the extraction engine 112 with examples of relevant assertions 108. Block 202 might also involve subject matter experts (and/or others) reviewing the results of previous attempts by the extraction engine 112 to extract assertions 108 from the text of publications 110 and providing feedback to the extraction engine 112 to improve its performance. In other words, it is contemplated that, in some embodiments, the blocks 202-206 may be performed iteratively as part of training the extraction engine 112 to recognize assertions 108 relevant to the particular biological field. In block 204, one or more publications 110 are selected to be input to the extraction engine 112 for the extraction of assertions 108 from the text of those publications 110. In some embodiments, block 204 may involve subject matter experts selecting peer-reviewed articles 110 from the relevant biological field that should be input to the extraction engine.

After block 204, the method 200 proceeds to block 206 in which the extraction engine 112 automatically extracts a plurality of assertions 108 from the publications 110. In some embodiments, the extraction engine 112 may include natural language processing software 112 to derive the assertions 108 from the text of the publications 110. In one illustrative embodiment, the natural language processing software 112 may be embodied as the K-Platform Extractor™, commercially available from Lymba Corporation of Richardson, Tex. As discussed above, in the illustrative embodiment, each of the assertions 108 extracted by the natural language processing software 112 is expressed as an RDF triple that encodes a relationship between a subject and an object (see FIG. 1). In some embodiments of method 200, block 206 may also involve automatically extracting one or more called biological sequences 114 from the publications 110. For instance, when the extraction engine 112 detects an assertion 108 in the one of the publications 110, the extraction engine 112 may then search for called biological sequences 114 set forth in the publication as examples of that assertion 108.

After block 206, the method 200 proceeds to block 208 in which the custom knowledgebase 100 is constructed using the assertions 108 that were automatically extracted from the publications 110 (during block 206). As illustrated in FIG. 2, block 206 also involves block 208, in which the automatically extracted assertions 108 are manually edited (e.g., by one or more subject matter experts in the particular biological field to which the custom knowledgebase 100 is directed). It is contemplated that the manual editing of the assertions 108 in block 208 may involve a number of tasks, including, but not limited to, selecting a subset of the assertions 108 automatically extracted from the publications 110 for inclusion in the custom knowledgebase 100 (or, alternatively, deleting the assertions 108 that should not be included in the custom knowledgebase 100), modifying the content of one or more of the assertions 108 automatically extracted from the publications 110, and/or creating one or more additional assertions 108 for inclusion in the custom knowledgebase 100.

After block 206, the method 200 also proceeds to block 212 in which the sequence dataset 102 is constructed. In the illustrative embodiment shown in FIG. 2, block 212 involves constructing the sequence dataset 102 using the called biological sequences 114 that were automatically extracted from the publications 110 during block 206. In some embodiments, block 212 may also involve blocks 214, 216. In block 214, additional called biological sequences 114 are extracted from one or more publicly available databases 116 (e.g., an NCBI database). After block 214, the method 200 proceeds to block 216 in which the additional called biological sequences 114 extracted from the databases 116 are compared to the called biological sequences 114 extracted from the publications 110. Where one or more predetermined resemblance criteria between the additional called biological sequences 114 extracted from the databases 116 and the called biological sequences 114 extracted from the publications 110 are met, these called biological sequences 114 are grouped together.

After blocks 208 and 212 (and/or, in some embodiments, during blocks 208, 212), the method 200 proceeds to block 218 in which each called biological sequence 114 (or group of called biological sequences 114) is associated with one or more of the assertions 108 of the custom knowledgebase 100. In some embodiments, block 218 may involve manual editing of the associations between the called biological sequences 114 and the assertions 108 of the custom knowledgebase 100 (e.g., by subject matter experts). In other embodiments, the associations of the called biological sequences 114 with the assertions 108 may be partially or fully automated. For instance, an association between an assertion 108 and a called biological sequences 114 that are both automatically extracted from a publication 110 during block 206 may be maintained throughout the method 200.

While the method 200 has generally been described above in terms of newly constructing the custom knowledgebase 100 and the sequence dataset 102, it will be appreciated that the method 200 may also be utilized to curate or update the custom knowledgebase 100 and the sequence dataset 102 on an ongoing basis. For instance, new publications 110 may periodically be input to the extraction engine 112 to extract new assertions 108 and called biological sequences 114 in order to keep the custom knowledgebase 100 and the sequence dataset 102 up-to-date. Similarly, as additional called biological sequences 114 are periodically added to the publicly available databases 116, these additional called biological sequences 114 may be added to the sequence dataset 102.

Figure 3:
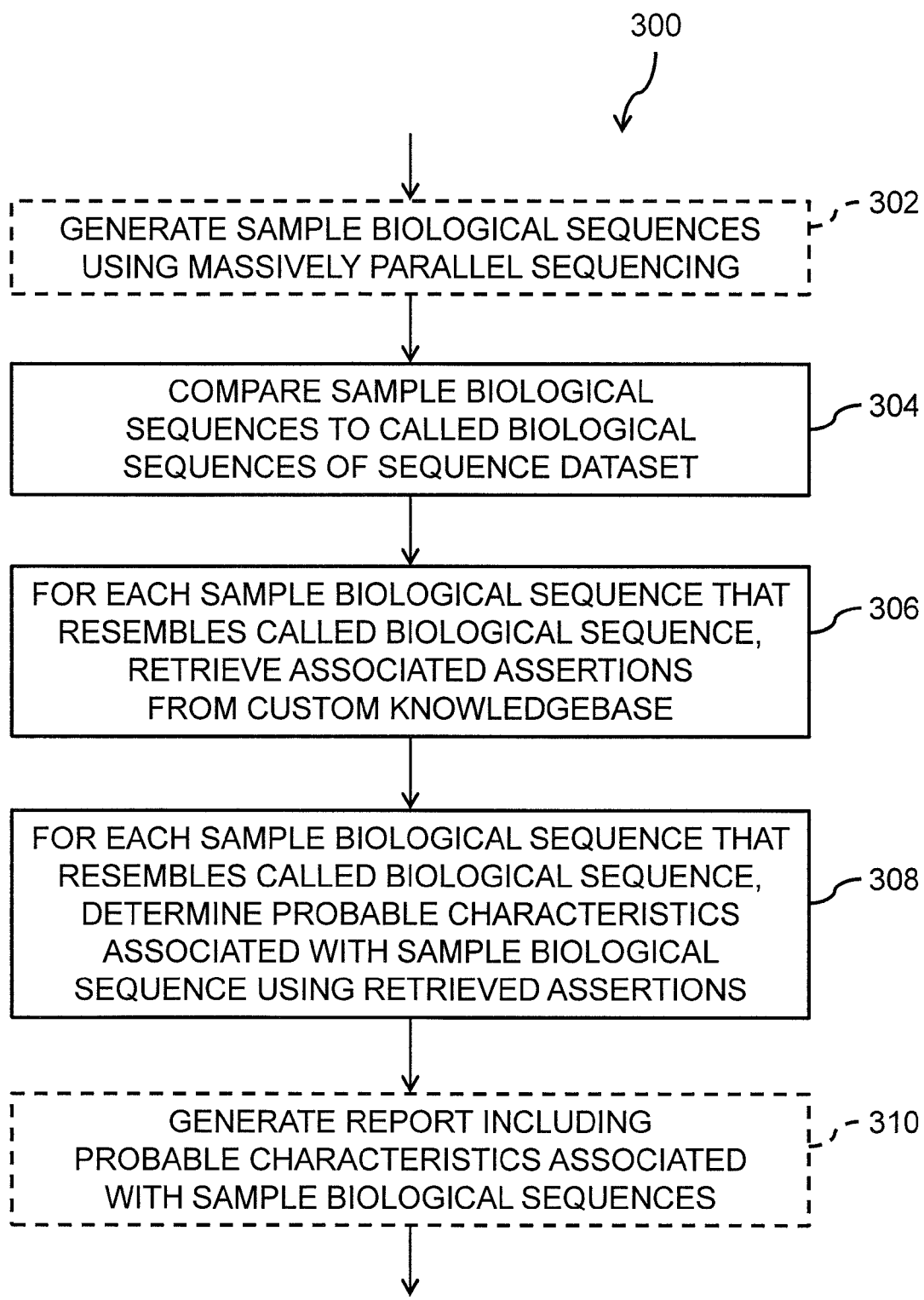
FIG. 3 is a simplified flow diagram illustrating one embodiment of a method of using the client application, the sequence dataset, and the custom knowledgebase of FIG. 1 to interrogate sample biological sequence data.

Referring now to FIG. 3, one illustrative embodiment of a method 300 of using the client application 104, the sequence dataset 102, and the custom knowledgebase 100 to interrogate the sample biological sequences 118 is shown as a simplified flow diagram. The method 300 is illustrated as a number of blocks 302-310. Although the blocks 302-310 are generally shown and described sequentially in the present disclosure, it will be appreciated that the blocks 302-310 do not necessarily need to be performed in a particular order (unless otherwise noted below). For instance, it is contemplated that many of the blocks 302-310 might be performed in parallel with other blocks during the method 300.

The method 300 begins with optional block 302 in which a plurality of sample biological sequences 118 are generated using MPS of a metagenomic sample. In other embodiments, where a data file (e.g., a FASTA or FASTQ format file) containing sample biological sequences 118 is received, the optional block 302 need not be performed as part of the method 300. In either case, the client application 104 receives sample biological sequences 118 (either from an MPS instrument or from a data file) prior to proceeding to block 304.

In block 304, the client application 104 communicates with the sequence dataset 102 to compare the sample biological sequences 118 to the called biological sequences 114 included in the sequence dataset 102. As a result of the comparisons performed in block 304, the client application 104 determines whether any of the sample biological sequences 118 resembles, or "matches," one or more of the called biological sequences 114. In some illustrative embodiments, an alignment algorithm (e.g., the BLAST algorithm) may be used to determine a degree of resemblance between each sample biological sequence 118 and each of the called biological sequences 114 included in the sequence dataset 102. Each sample biological sequence 118 may be "matched" to the called biological sequences 114 with the highest degree of resemblance, assuming the resemblance exceeds a threshold value. Alternatively, if a sample biological sequence 118 does not sufficiently resemble any of the called biological sequences 114, the client application 104 may determine that the sample biological sequence 118 has no matches in the sequence dataset 102. In other embodiments, the client application 104 may require exact matching between the sample biological sequences 118 and the called biological sequences 114 during block 304.

For each sample biological sequence 118 that is determined to resemble one of the called biological sequences 114 (during block 304), the method 300 proceeds to block 306 in which the client application 104 communicates with the custom knowledgebase 100 to retrieve one or more of the assertions 108. In particular, during block 306, the assertion(s) 108 that are associated with the called biological sequence 114 determined to resemble the sample biological sequence 118 are retrieved.

After block 306, the method 300 proceeds to block 308 in which the assertions 108 retrieved from the custom knowledgebase 100 (in block 306) are used to determine one or more probable characteristics associated with the sample biological sequence 118. The resemblance between the sample biological sequence 118 and the called biological sequence 114 in combination with the assertions 108 associated with the called biological sequence 114 allow the custom knowledgebase 100 to be used to infer information about the sample biological sequence 118. In the illustrative embodiment, block 308 may involve determining one or more antibiotics likely to be resisted by the sample from which the sample biological sequences 118 were read. Like block 306, block 308 is performed for each sample biological sequence 118 that was determined (in block 304) to resemble one of the called biological sequences 114.

The method 300 may conclude with optional block 310 in which a report 120 is generated that includes the probable characteristic(s) determined to be associated with the sample biological sequences 118 (in block 308). In the illustrative embodiment, the report 120 includes a ranked listing of antibiotics that are likely to be resisted by the sample (as determined in block 308). As noted above, the report 120 may list a number of antibiotics beginning with those with the most resistance elements present in the sample and concluding with those with the fewest (or no) resistance elements present in the sample. It will be appreciated that, in other embodiments, alternative formats for the report 120 may be used.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A method comprising:
automatically extracting a plurality of assertions from a plurality of publications, wherein each of the plurality of assertions encodes a relationship between a subject and an object;
manually editing the plurality of assertions automatically extracted from the plurality of publications to construct a custom knowledgebase for a particular biological field; and
constructing a sequence dataset comprising a plurality of called biological sequences, wherein each of the plurality of called biological sequences is associated with one or more of the plurality of assertions of the custom knowledgebase, wherein constructing the sequence dataset comprises:
automatically extracting one or more called biological sequences from the plurality of publications;
extracting additional called biological sequences from one or more publicly available databases;
grouping the additional called biological sequences with the one or more called biological sequences automatically extracted from the plurality of publications in response to one or more predetermined resemblance criteria being met; and
associating each group of called biological sequences with one or more of the plurality of assertions of the custom knowledgebase.

2. The method of claim 1, wherein manually editing the plurality of assertions automatically extracted from the plurality of publications comprises at least one of (i) selecting a subset of the plurality of assertions automatically extracted from the plurality of publications for inclusion in the custom knowledgebase, (ii) modifying the content of one or more of the plurality of assertions automatically extracted from the plurality of publications for inclusion in the custom knowledgebase, and (iii) creating one or more additional assertions for inclusion in the custom knowledgebase.

3. The method of claim 2, wherein the manual editing of the plurality of assertions automatically extracted from the plurality of publications is performed by one or more subject matter experts in the particular biological field.

4. The method of claim 3, wherein automatically extracting the plurality of assertions from the plurality of publications comprises utilizing natural language processing software to derive the plurality of assertions from the text of the plurality of publications.

5. The method of claim 4, wherein the plurality of publications comprise peer-reviewed articles selected by the subject matter experts.

6. The method of claim 4, wherein the natural language processing software has been trained by the subject matter experts to recognize relevant assertions in the text of the plurality of publications.

7. The method of claim 4, wherein each of the plurality of assertions is expressed as a Resource Description Framework (RDF) triple.

8. The method of claim 1, wherein the plurality of called biological sequences included in the sequence dataset and the associations between the plurality of called biological sequences and the plurality of assertions of the custom knowledgebase are manually edited by the subject matter experts.

9. One or more tangible, non-transitory computer-readable media comprising:
a custom knowledgebase comprising a plurality of assertions that have been automatically extracted from a plurality of publications, wherein each of the plurality of assertions encodes a relationship between a subject and an object;

a sequence dataset comprising a plurality of called biological sequences, wherein each of the plurality of called biological sequences is associated with one or more of the plurality of assertions of the custom knowledgebase; and a client application configured to:
compare a plurality of sample biological sequences to the plurality of called biological sequences of the sequence dataset; and determine, for at least one sample biological sequence that resembles a called biological sequence of the sequence dataset, one or more probable characteristics associated with that sample biological sequence using one or more assertions of the custom knowledgebase that are associated with the called biological sequence that resembles that sample biological sequence, wherein the at least one sample biological sequence is not in the sequence dataset.

10. The one or more tangible, non-transitory computer-readable media of claim 9, wherein the plurality of assertions automatically extracted from the plurality of publications have also been manually edited by one or more subject matter experts in a biological field of the custom knowledgebase.

11. The one or more tangible, non-transitory computer-readable media of claim 9, wherein:
the plurality of called biological sequences of the sequence dataset comprise at least one of called biological sequences that provide resistance to one or more antibiotics and called biological sequences that mediate regulation of antibiotic resistance; and
the plurality of assertions of the custom knowledgebase comprise assertions that encode relationships between the called biological sequences of the sequence dataset and at least one of antibiotic resistance elements and regulatory elements.

12. The one or more tangible, non-transitory computer-readable media of claim 11, wherein the plurality of assertions of the custom knowledgebase further comprise assertions that encode relationships between antibiotic resistance elements and particular resisted antibiotics.

13. A method comprising:
comparing a plurality of sample biological sequences to a plurality of called biological sequences included in a sequence dataset;
retrieving, from a custom knowledgebase associated with the sequence dataset, one or more assertions that are associated with a called biological sequence of the sequence dataset that resembles one of the plurality of sample biological sequences, wherein the one of the plurality of sample biological sequences is not in the sequence dataset and wherein the custom knowledgebase comprises a plurality of assertions that have been automatically extracted from a plurality of publications, each of the plurality of assertions encoding a relationship between a subject and an object; and
determining one or more probable characteristics associated with the sample biological sequence that resembles the called biological sequence of the sequence dataset using the one or more assertions retrieved from the custom knowledgebase.

14. The method of claim 13, wherein the plurality of assertions automatically extracted from the plurality of publications have also been manually edited by one or more subject matter experts in a biological field of the custom knowledgebase.

15. The method of claim 13, further comprising generating the plurality of sample biological sequences using massively parallel sequencing of a metagenomic sample.

16. The method of claim 13, wherein determining one or more probable characteristics associated with the sample biological sequence comprises determining one or more antibiotics likely to be resisted.

17. The method of claim 16, further comprising generating a report that comprises a ranked listing of the antibiotics likely to be resisted.

* * * * *